United States Patent [19]

Hayes, Jr. et al.

[11] 4,335,597
[45] Jun. 22, 1982

[54] DEW POINT HYGROMETER WITH TWO COOLED REFLECTIVE SURFACES

[75] Inventors: Stanley B. Hayes, Jr., Norfolk; Robert T. O'Connor, Holliston, both of Mass.

[73] Assignee: EG & G, Inc., Wellesley, Mass.

[21] Appl. No.: 134,827

[22] Filed: Mar. 28, 1980

[51] Int. Cl.³ ............................................. G01N 25/68
[52] U.S. Cl. .................................................. 73/17 A
[58] Field of Search ................... 73/17 A, 336, 336.5, 73/29

[56] References Cited

U.S. PATENT DOCUMENTS

| | | | |
|---|---|---|---|
| 2,624,195 | 1/1953 | Van Alen | 73/17 A |
| 2,714,818 | 8/1955 | Donsky et al. | 73/17 A |
| 3,077,763 | 2/1963 | Gena et al. | 73/17 A |
| 3,142,986 | 8/1964 | Wood et al. | 73/17 A X |
| 3,195,345 | 7/1965 | Thiele | 73/17 A |
| 3,252,319 | 5/1966 | Wood et al. | 73/17 A |
| 3,280,618 | 10/1966 | Ballinger | 73/17 A |
| 3,281,814 | 10/1966 | Roth | 73/17 A X |

FOREIGN PATENT DOCUMENTS

| | | | |
|---|---|---|---|
| 1165544 | 6/1958 | France | 73/17 A |
| 737658 | 9/1955 | United Kingdom | 73/17 A |

*Primary Examiner*—Charles A. Ruehl
*Attorney, Agent, or Firm*—Finnegan, Henderson, Farabow, Garrett and Dunner

[57] ABSTRACT

A dew point hygrometer which employs two cooled reflective surfaces with one surface being held at a lower temperature than the other. The lower temperature surface provides a wet mirror to detect dew formation and the dry mirror provides a standard which may be used to compensate for contamination build up on both surfaces.

8 Claims, 7 Drawing Figures

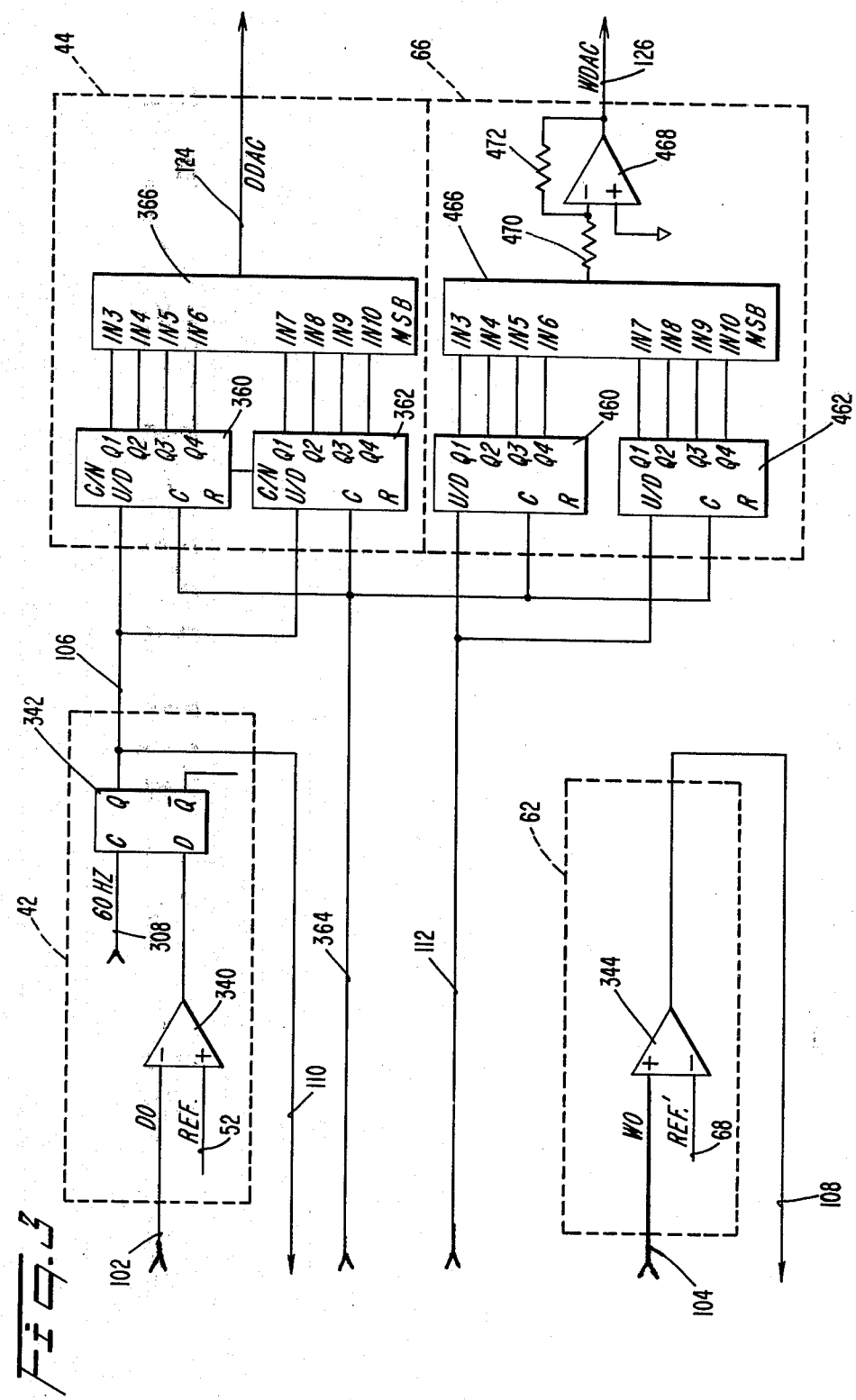

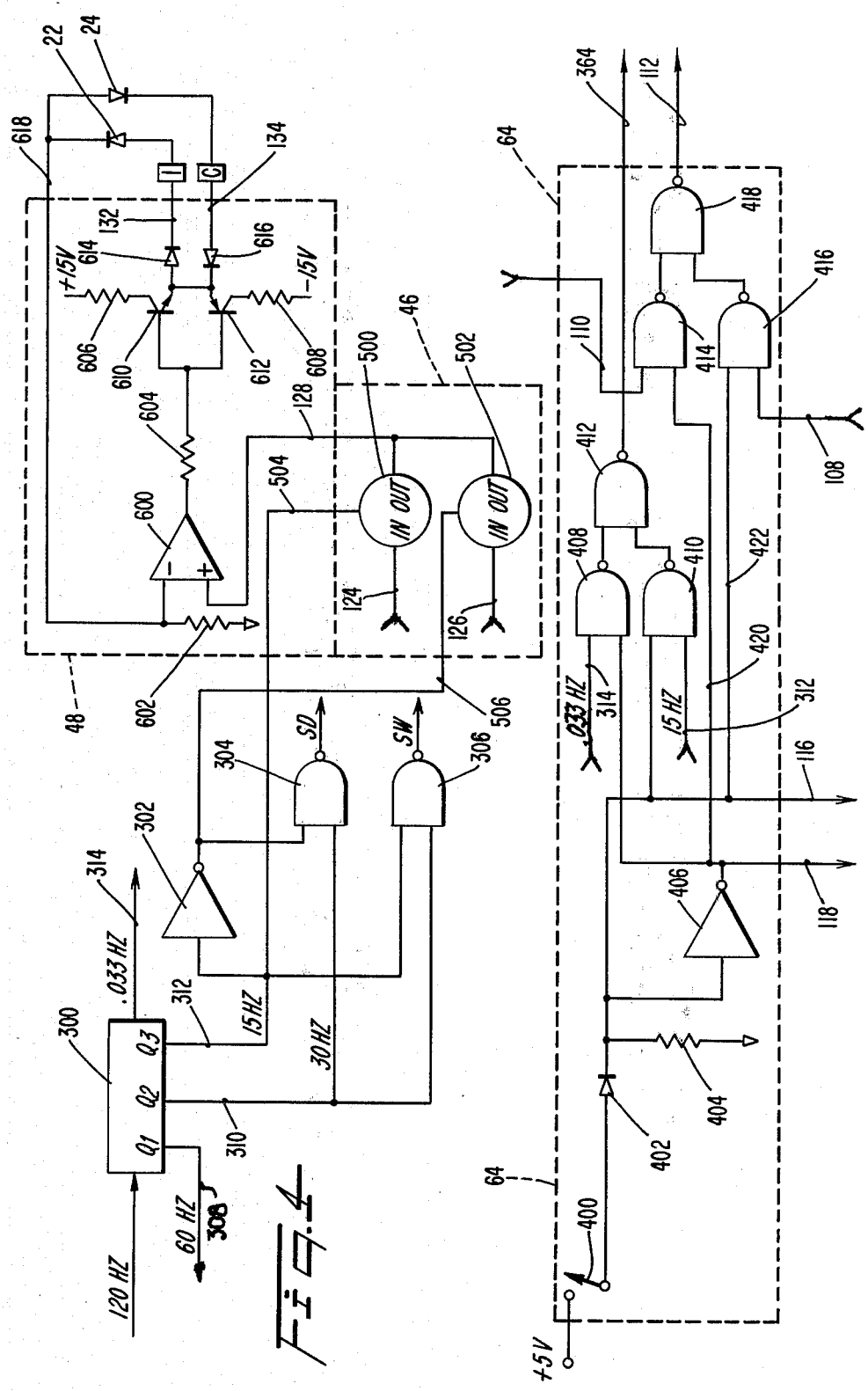

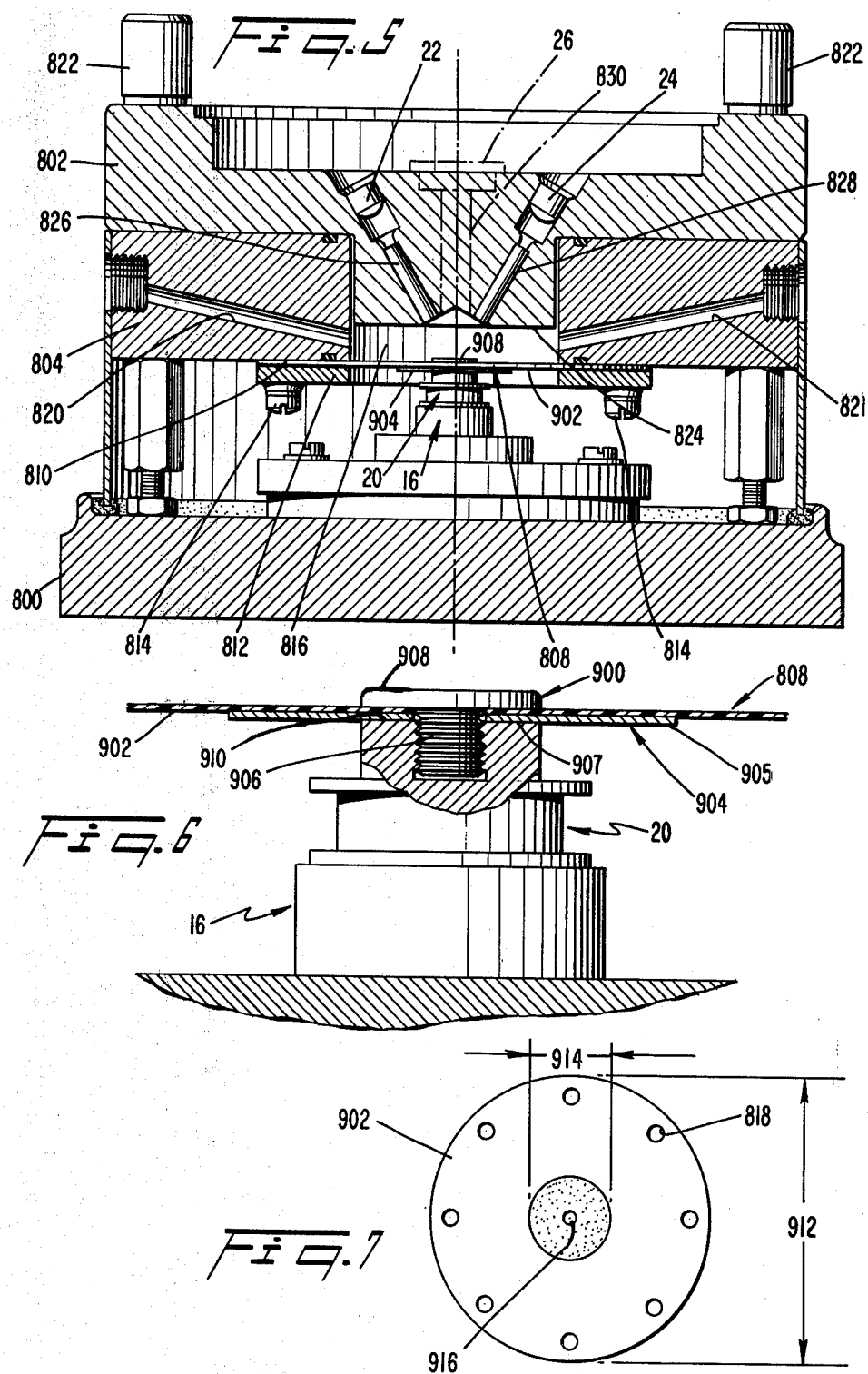

DEW POINT HYGROMETER WITH TWO COOLED REFLECTIVE SURFACES

BACKGROUND OF THE INVENTION

I. Field of the Invention

The present invention relates to an apparatus for detecting the presence of dew on a chilled mirror.

II. Description of the Prior Art

As is explained in U.S. Pat. No. 3,623,356 issued to Bisberg and assigned to the assignee of the present application, dew point hygrometers are frequently employed for determining the dew point of a gas sample. Typically, a single mirror is exposed to the gas sample, and the formation of dew thereon is detected by means of a light sensitive detector responsive to the light reflected therefrom. The light sensitive detector develops an error signal which is used to control the cooling current provided to a thermoelectric cooling device associated with the mirror to maintain the mirror at the dew point and, thus, maintain a predetermined thickness of condensation on the mirror surface. A temperature measuring device is employed for measuring the temperature of the mirror, thus giving an indication of the dew point of the gas sample.

In conventional prior art dew point hygrometers, condensation is sensed by the change of light reflected from a mirror surface. As contamination builds up on the mirror surface causing an additional reduction in the light level, the hygrometer responds by reducing the level of condensation until eventually there is no longer any condensation and all of the reduction in light level is due to contamination. At this point, the hygrometer erroneously reads a temperature above the dew point of the gas sample.

Accordingly, it has been necessary to periodically rebalance prior art dew point hygrometers to compensate for changes in the reflective characteristics of the mirror due to the accumulation of contamination. The Bisberg patent discloses one effective manner of automatically compensating for build-up of contamination on the reflective surface of a hygrometer mirror whereby the single mirror is periodically raised in temperature above the dew point, and the amount of reflection measured after evaporation of all dew from the mirror is used to indicate the degree of contamination present on the mirror surface.

Other prior art dew point hygrometers attempt to compensate for contamination build-up by employing a second mirror surface maintained at an ambient temperature with a second light sensitive element positioned to receive reflected light rays from the second mirror surface. The second mirror surface and second light sensitive element are used to provide an indication of the amount of contamination on a first mirror surface which is being cooled to detect dew point in the standard manner.

Athough a substantial advancement over the then existing prior art, the Bisberg dew point hygrometer does require periodic heating of a single mirror which interrupts the operation of the hygrometer. Furthermore, dual mirror hygrometers operate on the assumption that the mirror left at ambient temperature collects contamination at the same rate as the cool mirror. Furthermore, dual mirror hygrometers require separate light sensing circuits for each mirror, and any variation in the operation of either circuit creates an undesirable error in dew point measurement. As a result, prior art dew point hygrometers have only limited capacity to provide continuous dew point measurement automatically over an extended period of time.

It is, therefore, an object of the present invention to provide a mirror arrangement for a dew point hygrometer which allows for continuous compensation for contaminate build-up.

Another object of the present invention is to provide a mirror arrangement for a dew point hygrometer which allows for continuous compensation for contaminate build-up and yet provides for highly accurate dew point measurement.

A further object of the present invention is to provide a mirror arrangement for a dew point hygrometer which allows for compensation for contamination build-up and yet automatically provides for continuous unattended dew point measurement over extended periods of time.

Additional objects and advantages of the invention will be set forth in part in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, a dew point hygrometer is provided which comprises first and second reflective surfaces; means for cooling both the first and second reflective surfaces; means for maintaining the second surface at a lower temperature than the first surface; and means for reflecting light off the first and second reflective surfaces to detect the formation of dew on the second surface.

In a more narrow sense, applicants' invention comprises a dew point hygrometer having a thermally variable surface; first thermally conductive material having a first portion in contact with the surface and having a second portion extending beyond the surface; thermally insulative material covering at least a section of said first portion of the first material; second thermally conductive material covering at least a part of the section of the first portion of the first material; and means for reflecting light off the second portion of the first material and off the second material to detect the formation of dew on the second material.

It is preferable that the thermally insulative material comprises a sheet of polyester film which extends beyond the thermally variable surface. It is also preferable that at least a portion of the sheet of polyester film covering the first reflective sheet overlying the reflective sheet is transparent.

Preferably the first material comprises a reflective sheet positioned between the sheet of polyester film and the thermally variable surface with the first reflective sheet extending beyond the thermally variable surface, and at least a portion of the sheet of polyester film covering the first reflective sheet overlying said reflective sheet is transparent. The sheet of polyester film may extend beyond the reflective sheet and the second material may comprise a thermally conductive button having a reflective area positioned directly over the thermally variable surface, and the button preferably has means for thermally coupling the reflective area to the thermally variable surface.

Each of the above described dew point hygrometers preferably further includes a housing wherein the outside edge of the thermally insulative material is coupled to the housing to form a sample chamber comprising the housing and the thermally insulative material.

BRIEF DESCRIPTION OF THE DRAWINGS

The accompanying drawings, which are incorporated and constituted a part of the specification, illustrate a preferred embodiment of the invention and, together with the general description of the invention given above and the detailed description of the preferred embodiment given below, serve to explain the principles of the invention.

FIGS. 2, 3 and 4 illustrate a schematic diagram of the circuitry of a dew point hygrometer which is generally illustrated in FIG. 1;

FIG. 5 is structural diagram of a dew point hygrometer incorporating the teachings of the present invention;

FIG. 6 is a structural diagram of reflective surfaces incorporating the teachings of the present invention; and FIG. 7 illustrates a portion of the dew point hygrometer shown in FIG. 5 including an illustration of one reflective surface.

The above general description and the following detailed description are merely illustrative of the generic invention, and additional modes, advantages, and particulars of this invention will be readily suggested to those skilled in the art without departing from the spirit and scope of the invention.

DESCRIPTION OF THE PREFERRED EMBODIMENT

Reference will now be made in detail to the present preferred embodiment of the invention as described in the accompanying drawings.

Figure 1:
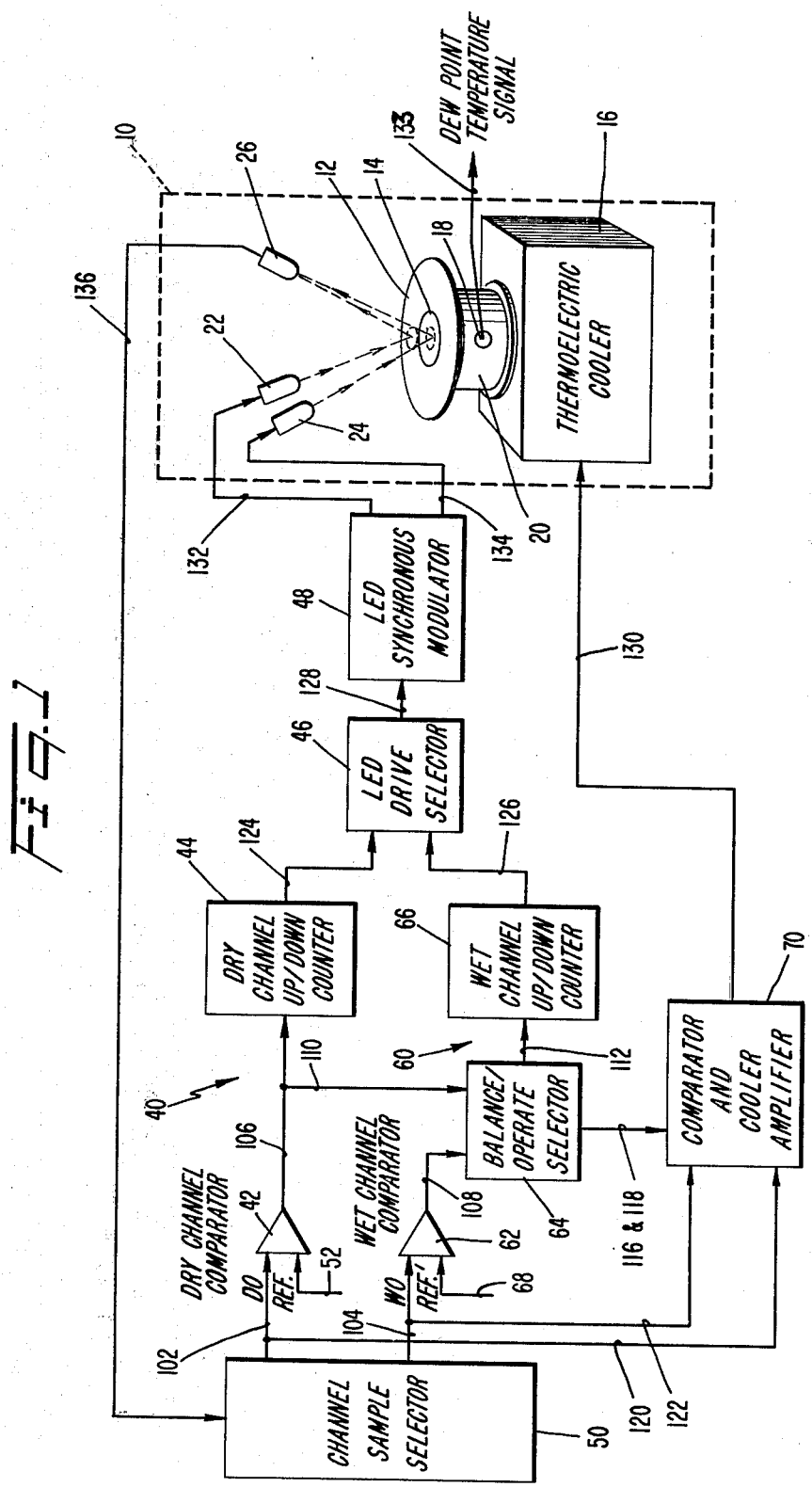
FIG. 1 is a block diagram of a dew point hygrometer which illustrates a circuit suitable for use with the present invention.

In FIG. 1 there is shown a block diagram which illustrates a preferred embodiment of a dew point hygrometer practicing the teachings of the present invention. In FIG. 1 a sensor 10 is illustrated comprising a first reflective surface 12 which may be referred to as dry mirror 12, a second reflective surface 14 which may be referred to as wet mirror 14, a cooler 16, a temperature sensor or thermometer 18, a temperature sensor holder 20, dry light emitting diode, LED 22, wet LED 24, and light sensor 26.

A detailed description of the structure of sensor 10 is set forth below with respect to FIGS. 5, 6 and 7. It is sufficient at this point to merely understand that dry mirror 12 and wet mirror 14 are positioned to reflect light from dry LED 22 and wet LED 24, respectively, to light sensor 26. Cooler 16 is preferably a thermoelectric cooler and is operated in response to a control signal received over line 130 to vary the temperature of temperature sensor holder 20. Wet mirror 14 is positioned in direct thermal contact with holder 20 and, hence, varies in temperature according to the temperature of holder 20.

Temperature sensor 18 is mounted in thermal contact with holder 20 and, accordingly, temperature sensor 18 provides over line 133 a signal indicating the temperature of holder 20 and wet mirror 14. Temperature sensor 18 may, for example, comprise a platinum resistance thermometer located in temperature sensor 20 just beneath the surface of wet mirror 14. A standard resistance to voltage converter may be coupled to sensor 18 in order to accurately measure the temperature of holder 20 and wet mirror 14.

Both mirrors 12 and 14 are mounted on an exposed surface of holder 20 in a manner, as is explained below with respect to FIGS. 5, 6 and 7, which provides for the cooling of both mirrors 12 and 14 while maintaining wet mirror 14 at a lower temperature than the temperature of dry mirror 12. Accordingly, condensation will tend to form on the surface of wet mirror 14 before condensation forms on the surface of dry mirror 12. Thus, wet mirror 14 acts in the conventional manner as a normal chilled mirror that is chilled to a dew point or the frost point of a gas sample and actually collects moisture as in the prior art. Dry mirror 12 is also chilled, but not to the same degree and, hence, remains dry. Dry mirror 12 is preferably held at approximately 10 degrees Celsius higher than the temperature of wet mirror 14.

By being held at nearly the same temperatures, the physical forces which cause wet mirror 14 to attract particulate matter, especially very light particulate matter such as dust and other foreign substances which may be in a gas sample whose dew point is being measured, also affect dry mirror 12 in a similar manner.

Furthermore, it should be noted that wet mirror 14 and dry mirror 12 are positioned in close physical and thermal proximity to one another. The physical and thermal proximity ensures both mirrors 12 and 14 will receive substantially the same amount of contaminates, more so than two mirrors physically separated or thermally separated where one is kept at an ambient temperature and the other is cooled to a dew point.

In order to detect condensation developed on wet mirror 14, and in order to utilize dry mirror 12 as a standard to measure contamination of the two mirrors, LED 24 is positioned to reflect light off wet mirror 14 into light sensor 26 and LED 22 is positioned to reflect light off a portion of dry mirror 12 into light sensor 26. By using two separate light sources but one light detector, any changes in the detection circuitry, which is more sensitive than the circuitry used to drive LEDs 22 and 24, are automatically compensated for as will be made more evident in the following discussion.

Dry LED 22 is driven by a signal received over line 132 and wet LED 24 is driven by a signal received over line 134. The output of light sensor 26 is provided on line 136. The circuit shown in FIG. 1 is responsive to the signals over line 136 from light sensor 26 to control the operation of cooler 16 by varying the signal delivered to cooler 16 over line 130. Furthermore, the circuit of FIG. 1 also shows one illustrative example of how LEDs 22 and 24 may be driven over lines 132 and 134 responsive to the output of light sensor 26 over line 136 to compensate for contamination of mirrors 12 and 14.

Specifically, dry LED 22 and wet LED 24 are alternately activated by signals over lines 132 and 134, respectively. When dry LED 22 is activated, any change in the contamination of dry mirror 12 is reflected in a corresponding change in the output of light sensor 26 over line 136. When wet LED 24 is activated by a signal over line 134, any change in the reflective qualities of wet mirror 14, due either to the presence of contamination, or the presence of condensation, is reflected by the output of light sensor 26 over line 136.

To measure dew point, the dew point hygrometer of FIG. 1 first enters a balance mode. In the balance mode LEDs 22 and 24 are driven to achieve an identical output of light sensor 26 with both dry mirror 12 and wet mirror 14 at a temperature sufficiently high to assure that no condensation has developed on wet mirror 14.

Thereafter, the dew point hygrometer enters an operate mode. In the operate mode, cooler 16 is activated to reduce the temperature of both mirrors 12 and 14, although a 10 degree differential is maintained between the mirrors. Cooler 16 continues to operate in response to a control signal over line 130 until the output of light sensor 26, upon activation of wet LED 24, varies by a selected amount from the output of light sensor 26, upon actuation of dry LED 22, sufficient to indicate the formation of condensation on wet mirror 14. However, to compensate for contamination build-up while this comparison operation is being carried out, the amount of drive signal supplied to wet LED 24 over line 134 is made dependent upon the amount of drive signal required on line 132 to maintain a predetermined output of light sensor 26 upon activation of dry LED 22.

To achieve the above described operation, there is shown in FIG. 1 a dry channel 40 comprising dry channel comparator 42, dry channel up/down counter 44, LED drive selector 46, and LED synchronous modulator 48. The input of channel 40 comprises a connection of line 136 from the output of light sensor 26 to an input of dry channel comparator 42 over line 102 by means of a channel sample selector 50. For simplicity of description, DO will refer to the signal from light sensor 26 when illuminated by a reflection of dry LED 22 off dry mirror 12. Thus, selector 50 operates to couple DO to a first input of comparator 42.

A second input to dry channel comparator 42 comprises a reference signal 52. Thus, dry channel comparator 42 compares DO with reference signal 52 and generates an output signal proportional to any differences between DO and reference signal 52. The output of dry channel comparator 42 is coupled by line 106 to the input of drive channel up/down counter 44 and stored in counter 44. More specifically, whenever an output signal from comparator 42 is present upon clocking of counter 44, counter 44 operates to store an additional count or remove a count depending upon the relationship between DO and reference signal 52. After initial balancing any change in DO is proportional to either a variation in the operation of light sensor 26 or increased contamination of dry mirror 12. Thus, after initial balancing the change in the number of counts stored in counter 44 is also proportional to the variations in light sensor 26 and the contamination of dry mirror 12.

The output of counter 44 is coupled by line 124 to an input of LED drive selector 46. The output of LED drive selector 46 is coupled by line 128 to the input of LED synchronous modulator 48, and an output of synchronous modulator 48 is coupled by line 132 to drive dry LED 22 responsive to the count stored in dry channel counter 44.

The circuit of FIG. 1 further includes a wet channel 60 comprising wet channel comparator 62, balance/operate selector 64, wet channel up/down counter 66, LED drive selector 46, and LED synchronous modulator 48. An input of wet channel comparator 62 is selectively connected to line 136 from light sensor 26 by channel sample selector 50 and line 104. For simplicity of description, WO will refer to the signal from light sensor 26 when illuminated by a reflection of wet LED 24 off wet mirror 14. Thus, selector 50 operates to couple WO to a first input of comparator 62. In a broad sense, selector 50 alternately couples light sensor 26 to comparators 42 and 62, as will be explained hereinafter.

A second input to wet channel comparator 62 is coupled to reference signal 68. Wet channel comparator 62 compares WO with reference signal 68 and generates an output signal proportional to any differences between WO and reference signal 68.

The output of wet channel comparator 62 is coupled by line 108 to an input of balance/operate selector 64 and the output of channel comparator 42 is also coupled over line 110 to an input of selector 64. One output of selector 64 is coupled over line 112 to the input of wet channel up/down counter 66 and another output of selector 64 is coupled over lines 116 and 118 to comparator and cooler amplifier 70. As will be described below, balance/operate selector 64 during the balance mode of operation, when both mirrors 12 and 14 are kept warm enough to prevent condensation, couples the output of wet channel comparator 62 to wet channel up/down counter 66. Thus, during the balance mode whenever an output signal from comparator 62 is present upon clocking of counter 66, counter 66 operates to store an additional count, or remove a count depending upon the relationship between WO and reference signal 68. In effect, during the balance mode, the count of counter 66 is set to assure a fixed initial illumination of wet LED 24. However, during the operate mode, selector 64 couples the output of dry channel comparator 42 to wet channel up/down counter 66, disconnects the output of wet channel comparator 62 from counter 66, and activates comparator and cooler amplifier 70. Thus, during operate mode, counter 66 is slaved to counter 44 and only changes in DO will result in changes in the illumination of LED 24. In effect, during the operate mode, only changes in DO will affect the count stored in wet channel counter 66.

The output of wet channel up/down counter 66 is coupled to LED drive selector 46 by line 126. As stated before, the output of LED drive selector 46 is coupled to the input of LED synchronous modulator 48. An additional output of LED synchronous modulator 48 is coupled by line 134 to wet LED 24.

The circuit of FIG. 1 further illustrates comparator and cooler amplifier 70 which has as inputs signal DO over line 120 and signal WO over line 122, and has an output coupled by line 130 to the input of cooler 16.

To balance the dew point hygrometer illustrated in FIG. 1, balance/operate selector 64 couples the output of wet channel comparator 62 on line 108 over line 112 to the input of wet channel up/down counter 66 and channel sample selector 50 alternately connects the output of light sensor 26 on line 136 to the inputs of dry channel comparator 42 and wet channel comparator 62. When connected to dry channel comparator 42 the output of light sensor 26, DO, is compared against reference signal 52 in dry channel comparator 42. The output of dry channel comparator 42 represents the degree by which output DO of light sensor 26 varies from reference 52. The channel sample selector 50 operates to connect light sensor 26 to an input of comparator 42 only when dry LED 22 is activated by LED synchronous modulator 48. Accordingly, the output of dry channel comparator 42 is proportional to the reflection caused by dry LED 22 off dry mirror 12.

With the output of comparator 42 coupled to the input of dry channel up/down counter 44, comparator 42 sets counter 44 responsive to the illumination of light sensor 26 by dry LED 22.

Channel sample selector 50 couples line 136 from light sensor 26 to an input of wet channel comparator 62 only upon activation of wet LED 24 by LED synchronous modulator 48. Furthermore, during the balance mode, balance/operate selector 64 simply connects the output of comparator 62 to wet channel up/down counter 66. Accordingly, during balance mode wet channel comparator 62 sets wet channel up/down counter 66 responsive to the illumination of light sensor 26 by wet LED 24. LED drive selector 46 translates the respective counts of dry counter 44 and wet counter 66 into an analog signal suitable for driving dry LED 22 and wet LED 24, respectively. LED synchronous modulator 48 couples the analog output from LED drive selector 46 to the respective LEDs 22 and 24 in synchronization with channel sample selector 50 as mentioned above.

Accordingly, channels 40 and 60 provide servo loops during the balance mode to maintain dry LED 22 and wet LED 24 driven to result in reflections off dry mirror 12 and wet mirror 14, respectively, in accordance with the values of references 52 and 68, respectively.

Once channels 40 and 60 have reached an equilibrium whereby the output over line 136 is in equilibrium with reference 52 during activation of dry LED 22 and the output of line 136 is in equilibrium with reference 68 during activation of wet LED 24, the circuit of FIG. 1 may enter the operate mode.

In the operate mode balance/operate selector 64 couples the output from the dry channel comparator 42 to the input of wet channel up/down counter 66, and balance/operate selector 64 further activates comparator and cooler amplifier 70. In the operate mode, any change in the reflective properties of dry mirror 12 will alter the output of light sensor 26 over line 136, and result in an imbalance in dry channel comparator 42 which is reported to counters 44 and 66, causing LED drive selector 46 to attempt to change the illumination of the dry LED 22 and wet LED 24 to offset the imbalance in comparator 42.

Comparator and cooler amplifier 70 is activated in the operate mode by selector 64, and compares signals DO and WO. Preferably reference signals 52 and 68 are chosen so that DO and WO are equal in magnitude and opposite in polarity during equilibrium in the absence of dew on wet mirror 14.

In the operate mode when comparator and cooler amplifier 70 detects that DO plus WO equals zero, comparator and cooler amplifier 70 operates to activate cooler 16. As stated above, cooler 16 reduces the temperature of both dry mirror 12 and wet mirror 14, but maintains wet mirror 14 at a lower temperature than dry mirror 12. The activation of cooler 16 continues until condensation forms on wet mirror 14, which causes a reduced output WO from light sensor 26, which reduced output results in a differential being created between the absolute values of WO and DO. This differential is detected by comparator and cooler amplifier 70, causing deactivation of cooler 16.

In this manner, a servo loop control is established which keeps the temperature of wet mirror 14 at the dew point of the gas being sampled.

The accumulation of contamination on dry mirror 12 and wet mirror 14 is compensated for by rendering wet channel up/down counter 66 responsive to the output of dry channel comparator 42. Specifically, during operate mode, the output of dry channel comparator 42 is coupled to the input of wet channel up/down counter 66 by balance/operate selector 64. Accordingly, any variation in the output of light sensor 26 during activation of dry LED 22, due to contamination of dry mirror 12 or variation in the operation of light sensor 26 is reported in both dry channel up/down counter 44 and wet channel up/down counter 66. Thus, the activation of wet LED 24 is slaved to the operation of dry LED 22. Due to the close physical and thermal proximity of dry mirror 12 and wet mirror 14, the slaving of wet LED 24 to dry LED 22 effectively compensates for contaminate build-up on mirrors 12 and 14.

With cooler 16 being operated to maintain wet mirror 14 at the dew point of the sample gas, the temperature of that dew point is easily detected by operation of temperature sensor 18.

Figure 2:
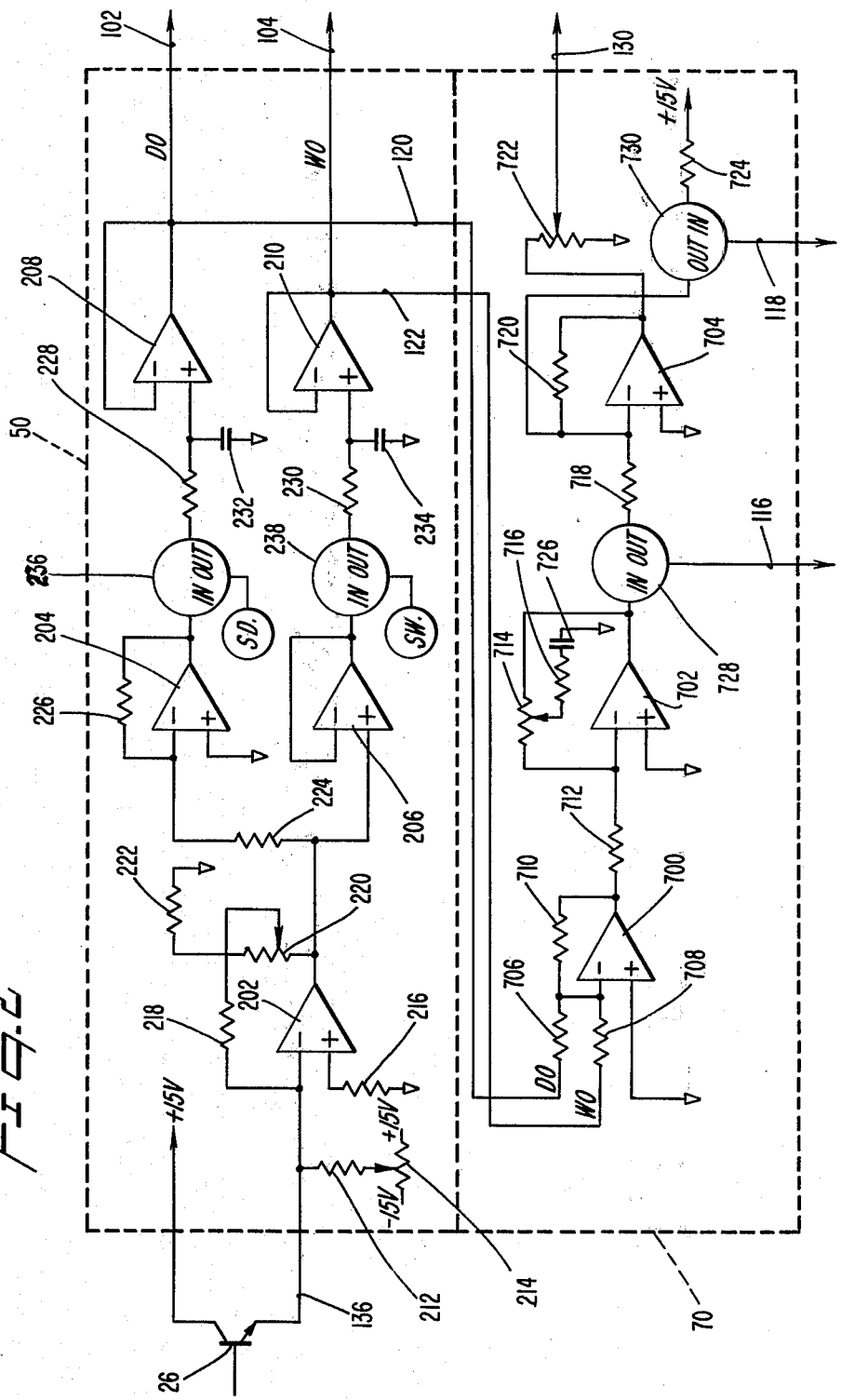

In FIGS. 2, 3 and 4, there is shown a more detailed schematic diagram of one example of the dew point hygrometer generally illustrated in FIG. 1.

In FIG. 2 light sensor 26 is illustrated in the form of a phototransistor having a collector connected to a 15 volt power supply and having an emitter connected by line 136 to channel sample selector 50. As stated above, channel sample selector 50 operates to couple the output of light sensor 26 alternately to the input of dry channel comparator 42 and the input of wet channel comparator 62. As illustrated in FIGS. 2 and 3, an output 102 of channel sample selector 50 is coupled to an input of dry channel comparator 42 shown in FIG. 3 and an output 104 of channel sample selector 50 is coupled to an input of wet channel comparator 62 shown in FIG. 3. An output of dry channel comparator 42 is coupled by line 106 to the input of dry channel up/down counter 44 and output of wet channel comparator 62 is coupled by line 108 to an input of balance/operate selector 64. Line 110 further couples the output of dry channel comparator 42 to an input of balance/operate selector 64 shown in FIG. 4.

Line 112 couples the output of balance/operate selector 64 to the input of wet channel up/down counter 66 shown in FIG. 3. Lines 116 and 118 further couple balance/operate selector 64 to comparator and cooler amplifier 70 as shown in FIG. 2. Comparator and cooler amplifier 70 receives an output DO from channel sample selector 50 over line 120 and further receives an output WO from channel sample selector 50 over line 122, whereas line 130 couples the output of comparator and cooler amplifier 70 to the input of cooler 16.

Returning to FIG. 3 there is shown a line 124 which couples the output of dry channel up/down counter 44 to an input of LED drive selector 46 illustrated in FIG. 4 whereas line 126 couples the output of wet channel up/down counter 66 to another input of LED drive selector 46. The output of LED drive selector 46 is coupled by line 128 to the input of LED synchronous modulator 48. The output of LED synchronous modulator 48 over line 132 drives dry LED 22 whereas the output of LED synchronous modulator 48 over line 134 drives wet LED 24.

It may therefore be seen that the schematic diagrams of FIGS. 2, 3, and 4 provide the same basic circuit elements illustrated in FIG. 1.

In FIG. 2 channel sample selector 50 is illustrated as comprising amplifiers 202, 204, 206, 208, 210, resistors 212, 214, 216, 218, 220, 222, 224, 226, 228, 230, capacitors 232 and 234, and switches 236 and 238.

Amplifier 202 has a negative input coupled directly to the emitter of phototransistor 26 and a positive input coupled to ground through resistor 216. Resistor 214 is shown coupled between a −15 volt source and +15 volt source. Resistor 214 has a variable tap which is coupled to the negative input of amplifier 202 by resistor 212. Accordingly, resistors 212 and 214 provide an offset bias for the input to amplifier 202.

The output of amplifier 202 is fed back to the input by the series combination of variable resistor 220 and resistor 218. Variable resistor 220 is further coupled to ground through resistor 222. In this connection, amplifier 202 provides an inverting amplifier for the output of phototransistor 26.

The output of amplifier 202 is also coupled directly to the input of amplifier 206 and is coupled to the input of amplifier 204 through resistor 224. The output of amplifier 204 is fed back to the input through resistor 226. Amplifiers 204 and 206 both provide buffering functions with amplifier 204 connected as a inverting buffer and amplifier 206 connected as a non-inverting buffer.

The outputs of amplifier 204 and 206 are coupled to the inputs of analog switches 236 and 238 respectively.

Analog switch 236 passes the output of amplifier 204 to resistor 228 upon activation by switching signal SD, whereas analog switch 238 passes the output of amplifier 206 to resistor 230 upon activation by switching signal SW. Switching signals SD and SW are in effect clocking signals and may be generated by circuitry illustrated in FIG. 4.

Specifically, the switching signals SD and SW are generated by counter 300, inverter 302, NAND gate 304, and NAND gate 306. Counter 300 is a binary counter and has as its input a 120 hertz clock and has as its output a 60 hertz signal on line 308, a 30 hertz signal on line 310, a 15 hertz signal on line 312, and 0.033 hertz signal on line 314. The 15 hertz signal on line 312 is coupled directly to an input of NAND gate 306 and is coupled through inverter 302 to an input of NAND gate 304. The 30 hertz signal on line 310 is coupled to an input of both NAND gates 304 and 306. The output of NAND gate 304 provides clock signal SD and the output of NAND gate 306 provides clock signal SW.

Returning now to FIG. 2, it may be seen that clock signal SD activates analog switch 236 to couple the output of amplifier 204 through resistor 228 to the input of amplifier 208, and clock signal SW activates analog switch 238 to couple the output of amplifier 206 through resistor 230 to the input of amplifier 210. The output of amplifier 208 on line 102 is the signal DO which varies as a function of the amount of light hitting phototransistor 26 upon activation of dry LED 22. The output of amplifier 210 on line 104 is the signal WO which varies as a function of the amount of light hitting phototransistor 26 upon activation of wet LED 24.

As stated above, lines 102 and 104 are coupled respectively to dry channel comparator 42 and wet channel comparator 62 illustrated on FIG. 3. In the example illustrated in FIG. 3, dry channel comparator 42 comprises amplifier 340 and a flip-flop 342. Wet channel comparator 62 merely comprises an amplifier 344. Amplifier 340 receives signal DO over line 102 at its negative input from amplifier 208 of channel sample selector 50. A positive reference signal 52 is shown supplied to the plus terminal of differential amplifier 340.

In a similar manner a negative reference signal 68 is coupled to the negative input terminal of amplifier 344.

Amplifiers 340 and 344 are preferably operational amplifiers which provide digital signals which are dependent upon the magnitude of input signals DO and WO in comparison to reference signal 52 and 68, respectively. Their outputs are used to control counters 44 and 66.

Flip-flop 342 in dry channel comparator 42 merely operates to serve as a delay to prevent an electronic "race" which might occur between counters 44 and 66 in the operate mode. It has been discovered that if the output of dry channel comparator 42 on line 106 is changing just as a clock pulse is being received by counters 44 or 66, a counter could be confused in the operate mode with one counter counting in one direction and the other counter counting in the other direction, in instances in which they both should have been counting in concert. The presence of flip-flop 342 at the output of differential amplifier 340 clocked by the 60 HZ signal on line 308 alleviates this problem.

Dry channel up/down counter 44 as shown in FIG. 3 comprises two four-stage binary counters 360 and 362. Binary counters 360 and 362 receive an input signal over line 106 from flip-flop 342 of dry channel comparator 42. Binary counters 360 and 362 also receive a clocking signal over line 364 from balance/operate selector 64 as will be explained in more detail below. The outputs of binary counters 360 and 362 are coupled to a digital to analog converter 366. Converter 366 generates an output signal, D-DAC, on line 124 which is a function of the count stored in counters 360 and 362. Output signal D-DAC is coupled through LED drive selector 46 and LED synchronous selector 48 of FIG. 1 to drive LED 22 until input signal DO on line 102 to dry channel comparator 42 reaches the value of reference 52.

The output of wet channel comparator 62 is coupled to the input of wet channel up/down counter 66 through balance/operate selector 64. As shown in FIG. 4, balance/operate selector 64 comprises switch 400, diode 402, resistor 404, inverter 406 and NAND gates 408, 410, 412, 414, 416, and 418. Switch 400 couples a +5 volt supply to the anode of diode 402. The cathode of diode 402 is coupled to ground through resistor 404 and is also coupled to one input of NAND gate 410. The other input of NAND gate 410 is coupled to the 15 hertz signal on line 312 from clock 300.

The cathode of diode 402 is also coupled through inverter 406 to an input of NAND gate 408. The second input of NAND gate 408 is coupled by line 314 to the 0.033 hertz output of clock 300.

The cathode of diode 402 is also coupled by line 116 to comparator and cooler amplifier 70 shown in FIG. 2 and the output of inverter 406 is coupled by line 118 to an input of comparator and cooler amplifier 70.

The outputs of NAND gates 408 and 410 are coupled to respective inputs of NAND gate 412 and the output of NAND gate 412 is coupled by line 364 to the clock inputs of binary counters 360 and 362 of dry channel up/down counter 44 in FIG. 3.

The output of inverter 406 is further coupled by line 420 to one input of NAND gate 414. A second input of NAND gate 414 is coupled by line 110 to the output of flip-flop 342 of dry channel comparator 42 in FIG. 3. Furthermore, the cathode of diode 402 is coupled by line 422 to an input of NAND gate 416. A second input of NAND gate 416 is coupled by line 108 to the output of wet channel comparator 62 in FIG. 3. The outputs of NAND gates 414 and 416 are coupled to respective inputs of NAND gate 418 and the output of NAND gate 418 is connected by line 112 to the input of wet channel up/down counter 66 in FIG. 3.

When switch 400 of balance/operate selector 64 is closed, the balance mode is entered. In the balance mode, a low signal $\overline{BI}$ appears on line 420 as input to NAND gate 414 and, accordingly, NAND gate 414 blocks any signal over line 110 from dry channel comparator 42 from reaching NAND gate 418. Furthermore, in the balance mode a signal BI on line 422 from the cathode of diode 402 is high, permitting NAND gate 416 to pass output signals on line 108 from wet channel comparator 62 to NAND gate 418 and subsequently over line 112 to the input of wet channel up/down counter 66.

However, when switch 400 is opened, the operate mode is entered in which the signal on line 420 is high, thereby permitting the output of dry channel comparator 42 to pass over line 110, through NAND gate 414, and through NAND gate 418 to wet channel up/down counter 66. Furthermore, in the operate mode the signal on line 422 from the cathode of diode 402 is low, thereby blocking NAND gate 416 from passing any signal over line 108 from wet channel comparator 62. It should be noted that the output of dry channel comparator 42 is continuously coupled to the dry channel up/down counter 44 by line 106 in both the balance and operate modes.

Accordingly, when in the balance mode, dry channel up/down counter 44 and wet channel up/down counter 66 operate independently in response to the outputs of dry channel comparator 42 and wet channel comparator 62, respectively. However in the operate mode, both dry channel up/down counter 44 and wet channel up/down counter 66 will operate in accordance with the output of dry channel comparator 42.

As shown in FIG. 3 wet channel up/down counter 66 may comprise two four-stage binary counters 460 and 462, digital-to-analog converter 466, amplifier 468, and resistors 470 and 472. The inputs to binary counters 460 and 462 are coupled by line 112 to the output of NAND gate 418 of balance/operate selector 64. Binary counters 460 and 462 are clocked by a clocking signal over line 364 in the same manner as binary counters 360 and 362 of dry channel up/down counter 44. The output of binary counters 460 and 462 are coupled to the input of digital-to-analog converter 466 and the output of digital-to-analog converter 466 is coupled by resistor 470 to the negative input of amplifier 468. A feedback resistor 472 is provided from the output of amplifier 468 to the negative input. The output of amplifier 468 provides an analog signal W-DAC which through LED drive selector 46 and LED synchronous modulator 48 drives wet LED 24 in the same manner that analog signal D-DAC on line 124 from dry channel up/down counter 44 drives dry LED 22.

Turning to FIG. 4, there is shown an example of LED drive selector 46 which comprises analog switches 500 and 502. Analog switch 500 has an input coupled to receive analog signal D-DAC over line 124 and an output coupled over line 128 to the input of LED synchronous modulator 48. Analog switch 500 has a control input coupled by line 504 to the 15 hertz output of clock 300.

Analog switch 502 receives analog signal W-DAC over line 126 and has an output connected by line 128 to the input of LED synchronous modulator 48. Analog switch 502 has a control input coupled by line 506 to the output of inverter 302. Analog switch 502 thereby operates in a complement manner to the operation of analog switch 500.

LED synchronous modulator 48 illustrated in FIG. 4 comprises amplifier 600, resistors 602, 604, 606, and 608, transistors 610 and 612, and diodes 614 and 616.

Amplifier 600 is coupled as a current source, receiving an input over line 128 from analog switches 500 and 502. The output of amplifier 600 is coupled through resistor 604 to the bases of transistors 610 and 612. Transistors 610 and 612 are coupled as current amplifiers, with the collector of transistor 610 coupled to a positive 15 volt source by resistor 606, the collector of transistor 612 coupled to a negative 15 volt source by resistor 608 and the emitters of transistors 610 and 612 coupled together.

Diode 614 couples the junctions of emitters 610 and 612 to the anode of dry LED 22 whereas diode 616 connects the common emitter junction of transistors 610 and 612 to the cathode of wet LED 24. The cathode of dry LED 22 and the anode of wet LED 24 are coupled by line 618 to ground through resistor 602. The junction of LEDs 22 and 24 and resistor 602 is coupled to the negative input of amplifier 600.

Accordingly, the output of amplifier 600 will assume whatever voltage is required to maintain the same voltage at its input terminals. Thus, if the cable length changes to LEDs 22 and 24, or if the forward ON voltage drop across LEDs 22 and 24 changes, there will still be the required amount of current flowing to LEDs 22 and 24 to accurately drive LEDs 22 and 24.

Comparator and cooler amplifier 70 is illustrated in FIG. 2 as comprising amplifiers 700, 702 and 704, resistors 706, 708, 710, 712, 714, 716, 718, 720, 722 and 724, capacitor 726, and analog switches 728 and 730.

Input signals DO and WO from channel sample selector 50 are coupled over lines 120 and 122 to resistors 706 and 708 of comparator and cooler amplifier 70. Resistors 706 and 708 are coupled together to provide the summation of signals DO and WO to the negative input of amplifier 700. The positive input of amplifier 700 is grounded, and the output of amplifier 700 is fed back to the negative input through resistor 710. Accordingly, amplifier 700 acts as summing amplifier of signals DO and WO.

The output of amplifier 700 is connected through resistor 712 to a negative input of amplifier 702. The positive input of amplifier 702 is coupled to ground, whereas the output of amplifier 702 is fed back to the negative input by resistor 714. Thus, resistors 712 and 714, and amplifier 702 form an inverting amplifier. Resistor 714 preferably has a variable tap which is coupled to ground through the series combination of resistor 716 and capacitor 726. Resistor 716 and capacitor 726 introduce a lead signal into the system of inverting amplifier 702 to overcome a phase lag which may result due to the time necessary for cooler 16 to react to a control signal over line 130 from comparator and cooler amplifier 70. The effect of resistor 716 and capacitor 726 is, however, dynamic and has no effect in steady state operation.

The output of amplifier 702 is coupled through the series combination of analog switch 728 and resistor 718 to the negative input of amplifier 704. The control terminal of analog switch 728 is coupled through line 116 to receive a high signal from the cathode of diode 402 in balance/operate selector 64 in the balance mode. Analog switch 728 opens in response to a high signal over line 116, and thereby deactivates comparator and cooler amplifier 70 in the balance mode by preventing the output of amplifier 702 from reaching the input of amplifier 704.

However, in the operate mode, a low signal is received over line 116, and analog switch 728 is thereby made conductive. The output of amplifier 702 is, accordingly, delivered to the input of amplifier 704 in the operate mode.

The positive input terminal of amplifier 704 is coupled to ground whereas the output is fed back to the negative input terminal of amplifier 704 by resistor 720. The negative input terminal of amplifier 704 is further coupled to a positive 15 volt supply through the series combination of analog switch 730 and resistor 724. The control terminal of analog switch 730 is coupled through line 118 to receive a low signal from the output of inverter 406 in balance/operate selector 64 during the balance mode. When in the balance mode, the low signal on line 118 closes analog switch 730 to provide a highly positive signal at the negative input of amplifier 704, which replaces the signal which otherwise would have appeared from amplifier 702 through analog switch 728. This highly positive signal causes a termination of cooling by cooler 16, and may in fact cause cooler 16 to heat up. This is important since during the balance mode it is necessary to have wet mirror 14 warm to prevent the formation of dew on wet mirror 14.

However, during the operate mode, a high signal is generated over line 118 and analog switch 730 is nonconductive. Thus, during the operate mode, the operation of amplifier 704 is governed solely by the output of amplifier 702.

The output of amplifier 704 is coupled through variable resistor 722 over line 130 to the input of thermoelectric cooler 16 in sensor 10 of FIG. 1.

In accordance with the present invention, the sensor of the present invention comprises first and second reflective surfaces; means for cooling both the first and second reflective surfaces; and means for maintaining the second surface at a lower temperature than the first surface.

A preferred embodiment of sensor 10 which incorporates the teaching of the present invention is illustratively shown in FIG. 5 as comprising a base 800, an optical housing 802, and an intermediate section 804. Cooler 16 of FIG. 1 is positioned in the center of base 800. As is also shown in FIG. 1 temperature sensor holder 20 is positioned above cooler 16, and an assembly 808 containing wet mirror 14 and dry mirror 12 is shown positioned above temperature sensor holder 20.

A better view of assembly 808 may be seen from FIGS. 6 and 7. Referring to FIG. 6, assembly 808 is shown to comprise a sensor button 900, a diaphragm 902, and a reflective disk 904.

Sensor button 900 is constructed of thermally conductive material. Sensor button 900 may, for example, be constructed of copper which contains a gold plating of approximately 0.00005 inches thick. The gold plating may be buffed lightly to provide a highly reflective surface 908 on the top of sensor button 900.

Temperature sensor holder 20 is preferably made of copper and has an exposed surface 910 which is thermally variable depending upon operation of cooler 16. Sensor button 900 has a projection 906 which extends through the thermally variable surface 910 of sensor holder 20 and engages the interior of sensor holder 20 in order to provide direct thermal connection between sensor holder 20 and reflective surface 908. Preferably, reflective surface 908 entirely covers, but does not extend over, thermally variable surface 910.

Positioned between reflective surface 908 and thermally variable surface 910 is the diaphragm 902. Diaphragm 902 is thermally insulative and may, for example, comprise a 5 millimeter thick polyester film. As is shown in FIG. 7, diaphragm 902 preferably assumes the shape of a circular disk having a diameter 912.

Diaphragm 902 is transparent, at least in the areas defined by diameter 914 as shown in FIG. 7. Diaphragm 902 may however contain a black screen extending from diameter 914 to the circumference of diaphragm 902. Diameter 914 may, for example, be on the order of 0.8 inches and diameter 912 may, for example, be on the order of 2.75 inches. A hole 916 in the center of diaphragm 902 must be of sufficient diameter to permit passage of projection 906 from sensor button 900 into temperature sensor holder 20.

Returning to FIG. 6, it may be seen that reflective disk 904 is positioned between diaphragm 902 and thermally variable surface 910. Reflective disk 904 is comprised of thermally conductive material and has a first portion 907 which is in contact with thermally variable surface 910, and a second portion 905 which extends beyond thermally variable surface 910. For example, reflective disk 904 may comprise 3M No. 7860 silver styrene, with 0.002 inch bright silver, an acrylic adhesive to attach disk 904 to diaphragm 902, and a Kraft release backing having a total thickness of approximately 0.005 inches. The center of a disk 904 has an opening to permit passage of projection 906 from reflective surface 908 into temperature sensor holder 20. Preferably, reflective disk 904 has the same diameter as the transparent diameter 914 of diaphragm 902.

With the above described arrangement, cooler 16 cools both reflective surface 908 and reflective disk 904. However, reflective surface 908 is maintained at a lower temperature than reflective disk 904, due both to the presence of diaphragm 902 which provides a heat sink for reflective disk 904 and due to the fact that reflective disk 904 extends beyond thermally variable surface 910 of temperature sensor holder 20.

Diaphragm 902 is directly connected to intermediate section 804 as illustrated in FIG. 5. Specifically, assembly 808 is positioned above base 800 at a height which permits engagement of the outside edge or circumference of disk 902 with a bottom surface 810 of intermediate section 804. A ring member 812 is positioned below diaphragm 902 and is attached to hold diaphragm 902 in connection with surface 810 through the use of a number of bolts 814 which pass through holes 818 of diaphragm 902.

Intermediate section 804 has an internal opening directly above assembly 808 which forms a sample gas chamber 816 which is directly exposed to reflective surface 908 of sensor button 900. However, chamber 816 is thermally isolated from reflective disk 904 by diaphragm 902. An input passage 820 is provided in intermediate section 804 in order to permit a gas sample to enter chamber 816. An exit passage 821 is also provided in intermediate section 804 in order to permit exit of a gas sample from chamber 816.

Optical housing 802 is firmly mounted on base 800 over intermediate section 804 by fasteners 822. Optical housing 802 has a lower surface 824 which forms the ceiling of gas chamber 816.

Optical housing 802 has mounted in it LEDs 22 and 24 and photosensor 26. FIG. 5 represents a cross sectional view of sensor 10 with the right half of FIG. 5 being a cross section of sensor 10 passing through LED 24 and the left half of FIG. 5 being a cross section of sensor 10 passing through LED 22. The interrelationship of LEDs 22 and 24, and photosensor 26 may be best appreciated from FIG. 1. Preferably, LEDs 22 and 24 are positioned adjacent one another, but separated by approximately 20 degrees.

Optical lenses 826, 828, and 830 assure that light from dry LED 22 strikes reflective disk 904, and reflects back into photosensor 26 and that light from wet LED 24 strikes reflective surface 908 and also reflects back into photosensor 26. Preferably the point of contact of light from dry LED 22 on reflective disk 904 is as close as possible to the point of contact of light from wet LED 24 on reflective surface 908. Preferably these points of contact may be on the order of only one-quarter of an inch apart.

Additional advantages and modification will readily occur to those skilled in the art. The invention in its broader aspects is therefore not limited to the specific details, representative apparatus, and the illustrative example shown and described. Accordingly, departures may be made from the detail without departing from the spirit or scope of the disclosed general inventive concept.

We claim:

1. A dew point hygrometer comprising:
   a. a thermally variable surface;
   b. first thermally conductive material having a first portion in contact with said surface and having a second portion extending beyond said surface;
   c. thermally insulative material covering at least a section of said first portion of said first material;
   d. second thermally conductive material covering at least a part of said section of said first portion of said first material; and
   e. means for reflecting light off said second portion of said first material and off said second material to detect the formation of dew on said second material.

2. The dew point hygrometer of claim 1 wherein said thermally insulative material comprises a sheet of polyester film.

3. The dew point hygrometer of claim 2 wherein said first material comprises a reflective sheet positioned between said sheet of polyester film and said thermally variable surface, and at least a portion of said sheet of polyester film overlying said reflective sheet is transparent.

4. The dew point hygrometer of claim 3 wherein said second material comprises a thermally conductive button having a reflective area positioned directly over said thermally variable surface, and having means for thermally coupling said reflective area to said thermally variable surface.

5. The dew point hygrometer of claim 1 wherein said thermally insulative material comprises a sheet of polyester film which extends beyond said thermally variable surface.

6. The dew point hygrometer of claim 5 wherein said first material comprises a reflective sheet positioned between said sheet of polyester film and said thermally variable surface with said reflective sheet extending beyond said thermally variable surface, and at least a portion of said sheet of polyester film overlying said reflective sheet is transparent.

7. The dew point hygrometer of claim 6 wherein said sheet of polyester film extends beyond said reflective sheet.

8. The dew point hygrometer of claims 1, 2, 5, 3, 6, 7 or 4 further including a housing wherein the outside edge of said thermally insulative material is coupled to said housing to form a sample chamber comprising said housing and said thermally insulative material.

* * * * *